United States Patent [19]

Schmidt et al.

[11] 4,424,225
[45] Jan. 3, 1984

[54] THIENOBENZODIAZEPINONES, PHARMACEUTICAL COMPOSITIONS THEREOF AND METHOD OF USE THEREOF

[75] Inventors: Günther Schmidt; Wolfgang Eberlein; Wolfhard Engel, all of Biberach; Günter Trummlitz, Warthausen, all of Fed. Rep. of Germany; Rudolf Hammer, Milan; Piero Del Soldato, Monza, both of Italy

[73] Assignee: Dr. Karl Thomae GmbH, Biberach an der Riss, Fed. Rep. of Germany

[21] Appl. No.: 462,379

[22] Filed: Jan. 31, 1983

[30] Foreign Application Priority Data

Feb. 6, 1982 [DE]   Fed. Rep. of Germany ....... 3204153

[51] Int. Cl.³ .................... C07D 513/04; A61K 31/55
[52] U.S. Cl. .................................. 424/256; 424/263; 424/267; 260/239.3 T
[58] Field of Search ................ 260/239.3 T; 424/256, 424/263, 267

[56] References Cited

U.S. PATENT DOCUMENTS 4,381,301   4/1983   Rainer ........................ 260/239.3 T

*Primary Examiner*—Robert T. Bond

*Attorney, Agent, or Firm*—Hammond & Litell, Weissenberger & Muserlian

[57] ABSTRACT

This invention relates to novel compounds of the formula

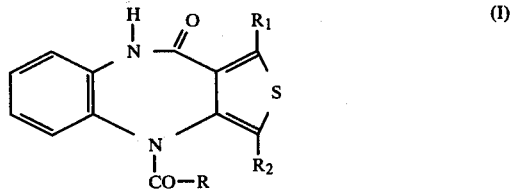

wherein $R_1$ is hydrogen or alkyl having from 1 to 4 carbon atoms;

$R_2$ is halogen, hydrogen, or alkyl having from 1 to 4 carbon atoms; and

R is (1-methyl-4-piperidinyl)methyl, (1-methyl-1,2,5,6-tetrahydro-4-pyridinyl)methyl, 1-methyl-1,2,5,6-tetrahydro-4-pyridinyl, (1-methyl-4-piperidinylidene)-methyl, or (8-methyl-8-azabicyclo[3.2.1]oct-3-yl)-methyl, each of which can optionally have an additional methyl substituent on the heterocyclic ring, and non-toxic, pharmacologically acceptable acid addition salts thereof. The compounds as well as their salts are useful as anti-ulcerogenics.

5 Claims, No Drawings

THIENOBENZODIAZEPINONES, PHARMACEUTICAL COMPOSITIONS THEREOF AND METHOD OF USE THEREOF

FIELD OF THE INVENTION

This invention relates to novel substituted thienobenzodiazepinones. More particularly, this invention relates to novel substituted thienobenzodiazepinones and non-toxic acid addition salts thereof, methods of preparing these compounds, pharmaceutical compositions containing them as active ingredients, and a method of using them as anti-ulcerogenics and gastric acid secretion inhibitors.

BACKGROUND OF THE INVENTION

In German Offenlegungsschrift No. 1,795,176, certain dibenzodiazepinones having anti-ulcerogenic and secretion-inhibiting properties are described. U.S. Pat. No. 3,953,430 discloses substituted dibenzodiazepines having antidepressant and analgesic properties, while U.S. Pat. No. 4,168,269 discloses substituted thienobenzodiazepines having analgesic properties. Moreover, thienobenzodiazepinones having anti-ulcerogenic and secretion-inhibiting properties are mentioned in published European Patent Application No. 0,039,519. Thienobenzodiazepinones with novel aminoacyl groups have now been found which have valuable pharmacological properties superior to those of the aforementioned compounds.

OBJECTS OF THE INVENTION

It is an object of the invention to provide novel substituted thienobenzodiazepinones having useful pharmacodynamic properties superior to those of the related compounds disclosed in the prior art.

It is also an object of the invention to provide pharmaceutical compositions containing substituted thienobenzodiazepinones as active ingredients.

It is a further object of the invention to provide a method of using substituted thienobenzodiazepinones as anti-ulcerogenics and gastic acid secretion inhibitors.

These and other objects of the invention will become more apparent from the discussion below.

DETAILED DESCRIPTION OF THE INVENTION

The present invention relates to a novel class of substituted thienobenzodiazepinones represented by the formula

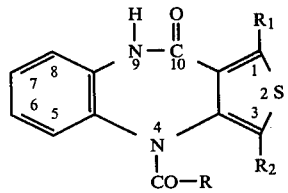

wherein $R_1$ is hydrogen or alkyl having from 1 to 4 carbon atoms;

$R_2$ is halogen or one of the meanings of $R_1$; and

R is a (1-methyl-4-piperidinyl)methyl, (1-methyl-1,2,5,6-tetrahydro-4-pyridinyl)methyl; 1-methyl-1,2,5,6-tetrahydro-4-pyridinyl, (1-methyl-4-piperidinylidene)methyl, or (8-methyl-8-azabicyclo[3.2.1]oct-3-yl)methyl, each of which may optionally have another methyl substituent attached to the heterocyclic six-membered ring, and pharmacologically acceptable acid addition salts thereof.

Alkyl groups having from 1 to 4 carbon atoms include methyl, ethyl, propyl, isopropyl, n-butyl, isobutyl, sec.-butyl, and tert.butyl groups, the methyl group being particularly preferred as an alkyl group for $R_1$ or $R_2$. The bromine atom, and particularly the chlorine atom, are preferred halogen atoms for $R_2$.

Particularly preferred compounds of Formula I are those wherein $R_1$ represents hydrogen or methyl;

$R_2$ represents chlorine, hydrogen, or methyl; and

R represents (1-methyl-4-piperidinyl)methyl, (1-methyl-1,2,5,6-tetrahydro-4-pyridinyl)methyl, 1-methyl-1,2,5,6-tetrahydro-4-pyridinyl, (8-methyl-8-azabicyclo[3.2.1]oct-3-yl)-methyl, or (1-methyl-4-piperidinylidene)methyl, or a pharmacologically acceptable acid addition salt thereof.

The compounds of Formula I may also be obtained in the form of their pharmacologically acceptable salts after being reacted with inorganic or organic acids. Suitable acids include, for example, hydrochloric, hydrobromic, sulfuric, methylsulfuric, phosphoric, tartaric, fumaric, citric, maleic, succinic, gluconic, malic, p-toluenesulfonic, methanesulfonic, and amidosulfonic acid.

The following compounds are illustrative of the invention:

(a) 4,9-dihydro-4-[(1-methyl-4-piperidinyl)acetyl]-10H-thieno[3,4-b][1,5]benzodiazepin-10-one;

(b) 4,9-dihydro-4-[(1,3-dimethyl-4-piperidinyl)acetyl]-10H-thieno[3,4-b][1,5]benzodiazepin-10-one;

(c) 4,9-dihydro-4-[(1,2-dimethyl-4-piperidinyl)acetyl]-10H-thieno[3,4-b][1,5]benzodiazepin-10-one;

(d) 4,9-dihydro-1-methyl-4-[(1-methyl-4-piperidinyl)acetyl]-10H-thieno[3,4-b][1,5]benzodiazepin-10-one;

(e) 4,9-dihydro-3-methyl-4-[(1-methyl-4-piperidinyl)acetyl]-10H-thieno[3,4-b][1,5]benzodiazepin-10-one;

(f) 4,9-dihydro-1,3-dimethyl-4-[(1-methyl-4-piperidinyl)-acetyl]-10H-thieno[3,4-b][1,5]benzodiazepin-10-one;

(g) 3-chloro-4,9-dihydro-4-[(1-methyl-4-piperidinyl)acetyl]-10H-thieno[3,4-b][1,5]-benzodiazepin-10-one;

(h) 4,9-dihydro-4-[(1-methyl-1,2,5,6-tetrahydro-4-pyridinyl)-acetyl]-10H-thieno[3,4-b][1,5]benzodiazepin-10-one;

(i) 4,9-dihydro-4-[(1,2-dimethyl-1,2,5,6-tetrahydro-4-pyridinyl)acetyl]-10H-thieno[3,4-b][1,5]benzodiazepin-10-one;

(j) 4,9-dihydro-4-[(1,3-dimethyl-1,2,5,6-tetrahydro-4-pyridinyl)acetyl]-1-methyl-10H-thieno[3,4-b][1,5]-benzodiazepin-10-one;

(k) 4,9-dihydro-4-[(1,5-dimethyl-1,2,5,6-tetrahydro-4-pyridinyl)acetyl]-10H-thieno[3,4-b][1,5]benzodiazepin-10-one;

(l) 4,9-dihydro-4-[(1,6-dimethyl-1,2,5,6-tetrahydro-4-pyridinyl)acetyl]-10H-thieno[3,4-b][1,5]benzodiazepin-10-one;

(m) 4,9-dihydro-1-methyl-4-[(1-methyl-1,2,5,6-tetrahydro-4-pyridinyl)acetyl]-10H-thieno[3,4-b][1,5]benzodiazepin-10-one;

(n) 4,9-dihydro-3-methyl-4-[(1-methyl-1,2,5,6-tetrahydro-4-pyridinyl)acetyl]-10H-thieno[3,4-b][1,5]benzodiazepin-10-one;

(o) 4,9-dihydro-1,3-dimethyl-4-[(1-methyl-1,2,5,6-tetrahydro-4-pyridinyl)acetyl]-10H-thieno[3,4-b][1,5]benzodiazepin-10-one;

(p) 3-chloro-4,9-dihydro-4-[(1-methyl-1,2,5,6-tetrahydro-4-pyridinyl)acetyl]-10H-thieno[3,4-b][1,5]benzodiazepin-10-one;

(q) 4,9-dihydro-4-[(1-methyl-1,2,5,6-tetrahydro-4-pyridinyl)-carbonyl]-10H-thieno[3,4-b][1,5]benzodiazepin-10-one;

(r) 4,9-dihydro-4-[(1,2-dimethyl-1,2,5,6-tetrahydro-4-pyridinyl)carbonyl]-10H-thieno[3,4-b][1,5]benzodiazepin-10-one;

(s) 4,9-dihydro-4-[(1,3-dimethyl-1,2,5,6-tetrahydro-4-pyridinyl)carbonyl]-10H-thieno[3,4-b][1,5]benzodiazepin-10-one;

(t) 4,9-dihydro-4-[(1,5-dimethyl-1,2,5,6-tetrahydro-4-pyridinyl)carbonyl]-1-methyl-10H-thieno[3,4-b][1,5]benzodiazepin-10-one;

(u) 4,9-dihydro-4-[(1,6-dimethyl-1,2,5,6-tetrahydro-4-pyridinyl)carbonyl]-10H-thieno[3,4-b][1,5]benzodiazepin-10-one;

(v) 4,9-dihydro-1-methyl-4-[(1-methyl-1,2,5,6-tetrahydro-4-pyridinyl)carbonyl]-10H-thieno[3,4-b][1,5]benzodiazepin-10-one;

(w) 4,9-dihydro-3-methyl-4-[(1-methyl-1,2,5,6-tetrahydro-4-pyridinyl)carbonyl]-10H-thieno[3,4-b][1,5]benzodiazepin-10-one;

(x) 4,9-dihydro-1,3-dimethyl-4-[(1-methyl-1,2,5,6-tetrahydro-4-pyridinyl)carbonyl]-10H-thieno[3,4-b][1,5]benzodiazepin-10-one;

(y) 3-chloro-4,9-dihydro-4-[(1-methyl-1,2,5,6-tetrahydro-4-pyridinyl)carbonyl]-10H-thieno[3,4-b][1,5]benzodiazepin-10-one;

(z) endo-4,9-dihydro-4-[(8-methyl-8-azabicyclo[3.2.1]oct-3-yl)acetyl]-10H-thieno[3,4-b][1,5]benzodiazepin-10-one;

(aa) exo-4,9-dihydro-4-[(8-methyl-8-azabicyclo[3.2.1]oct-3-yl)acetyl]-10H-thieno[3,4-b][1,5]benzodiazepin-10-one;

(bb) endo-4,9-dihydro-1-methyl-4-[(8-methyl-8-azabicyclo-[3.2.1]oct-3-yl)acetyl]-10H-thieno[3,4-b][1,5]benzodiazepin-10-one;

(cc) exo-4,9-dihydro-1-methyl-4-[(8-methyl-8-azabicyclo-[3.2.1]oct-3-yl)acetyl]-10H-thieno[3,4-b][1,5]benzodiazepin-10-one;

(dd) endo-4,9-dihydro-3-methyl-4-[(8-methyl-8-azabicyclo-[3.2.1]oct-3-yl)acetyl]-10H-thieno[3,4-b][1,5]benzodiazepin-10-one;

(ee) endo-4,9-dihydro-1,3-dimethyl-4-[(8-methyl-8azabicyclo-[3.2.1]oct-3-yl)acetyl]-10H-thieno[3,4-b][1,5]benzodiazepin-10-one;

(ff) endo-3-chloro-4,9-dihydro-4-[(8-methyl-8-azabicyclo-[3.2.1]oct-3-yl)acetyl]-10H-thieno[3,4-b][1,5]benzodiazepin-10-one;

(gg) 4,9-dihydro-4-[(1-methyl-4-piperidinylidene)acetyl]-10H-thieno[3,4-b][1,5]benzodiazepin-10-one;

(hh) 4,9-dihydro-1-methyl-4-[(1-methyl-4-piperidinylidene)-acetyl]-10H-thieno[3,4-b][1,5]benzodiazepin-10-one;

(ii) 4,9-dihydro-3-methyl-4-[(1-methyl-4-piperidinylidene)-acetyl]-10H-thieno[3,4-b][1,5]benzodiazepin-10-one;

(jj) 4,9-dihydro-1,3-dimethyl-4-[(1-methyl-4-piperidinylidene)-acetyl]-10H-thieno[3,4-b][1,5]benzodiazepin-10-one; and (kk) 3-chloro-4,9-dihydro-4-[(1-methyl-4-piperidinylidene)-acetyl]-10H-thieno[3,4-b][1,5]benzodiazepin-10-one.

The substituted thienobenzodiazepinones of Formula I and the acid addition salts thereof have valuable properties which make them commercially viable, and they are characterized in particular by an excellent protective effect on the stomach and intestines in warm-blooded animals. For example, they inhibit the formation of gastric ulcers. Moreover, they have a useful therapeutic range, due to their low toxicity and the absence of any significant side effects.

The excellent activity of the pharmacologically active compounds of Formula I and of their pharmacologically, i.e., biologically, acceptable acid addition salts makes it possible to use them in both human and veterinary medicine, for the treatment and prophylaxis of diseases based upon disorders of the stomach or intestines. They may be used, for example, to treat acute and chronic gastric and duodenal ulcers, gastritis, and gastric hyperacidity in humans and animals.

For such treatment, the compounds of Formula I and their pharmacologically acceptable salts can be incorporated, optionally in combination with other active ingredients, in manner known per se, into the usual pharmaceutical preparations such as tablets, coated tablets, capsules, powders, infusions, suppositories, solutions, or suspensions. The daily dose for adults is from about 0.75 to 375 mg (from about 0.01 to 5 mg/kg), preferably from about 1.5 to 188 mg (from about 0.02 to 2.5 mg/kg), more particularly, from about 3.75 to 75.0 mg (from about 0.05 to 1.0 mg/kg), generally administered in the form of several, preferably from 1 to 3, individual doses to achieve the desired results. Dependent upon the type and body weight of the patient to be treated, on the type and severity of the disease, on the type of preparation and on the route of administration as well as on the period or interval over which the administration takes place, it may, however, be necessary to deviate from the above dosages. Thus, it may be sufficient in some cases to administer more or less than the above-mentioned amounts of active ingredient. The optimum dosage and route of administration of the active ingredients which are necessary in each case can easily be determined by one skilled in the art.

The invention further relates to pharmaceutical compositions containing the compounds of Formula I. Similarly, the invention relates to the use of the compounds according to the invention in the preparation of pharmaceutical compositions used in the treatment of the diseases mentioned above.

If the substituted thienobenzodiazepinones of Formula I and/or the pharmacologically acceptable acid addition salts thereof are to be used to treat the diseases mentioned above, the pharmaceutical preparations may also contain one or more pharmacologically active components, i.e., active ingredients, from other groups of medicaments, such as antacids, e.g., aluminium hydroxide or magnesium aluminate; secretion-inhibitors such as H$_2$ blockers, e.g., cimetidine or ranitidine; gastric and intestinal therapeutic agents, e.g., metoclopramide, bromoprid, or tiaprid; tranquilizers such as benzodiazepines, for example, diazepam or oxazepam; spasmolytics, e.g., bietamiverine or camylofine; anticholinergics, e.g., oxyphencyclimine or phencarbamide; glucocorticoids such as prednisolone, fluocortolone, or betamethasone; non-steroidal antiphlogistic agents such as arylacetic acids, arylpropionic acids, heteroarylacetic acids, heteroarylpropionic acids, benzothiazine carboxamide dioxides, pyrazolidinediones, or quinazolinones, e.g., ibuprofen, naproxen, diclofenac, fenbufen, flurbiprofen, indomethacin, lonazolac, sudoxicam, piroxicam, phenylbutazone, bumadizon-calcium, or proquazone; and local anesthetics such as tetracaine or procaine. Optionally, enzymes, vitamins, amino acids, or the like, may also be present.

Another aspect of the invention relates to processes for the preparation of substituted thienobenzodiazepinones of Formula I as well as the acid addition salts thereof. These compounds can be prepared as follows:

METHOD A

All the compounds of Formula I can be prepared by acylating thienobenzodiazepinones of the formula

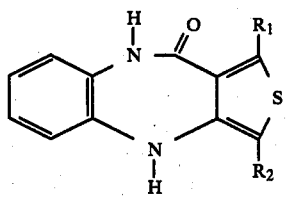
(II)

wherein $R_1$ and $R_2$ are as defined above, with acid derivatives of the formula

(III)

wherein R is as defined above and Z represents a nucleophobic group or a leaving group.

The reaction of the compounds of Formula II with the acid derivatives of Formula II is effected in a manner known per se. The leaving group Z is a group which, together with the carbonyl group to which it is bonded, forms a reactive carboxylic acid derivative. Examples of reactive carboxylic acid derivatives include acid halides, esters, anhydrides, and mixed anhydrides, as obtained from salts of the corresponding acid (Z=OH), and acid chlorides, such as phosphorus oxychloride, diphosphoric acid tetrachloride, or chloroformates, and the N-alkyl-2-acyloxy-pyridinium salts formed by reacting compound III (Z=OH) with N-alkyl-2-halo-pyridinium salts.

The reaction is preferably carried out with the mixed anhydrides of strong inorganic acids, particularly dichlorophosphoric acid. The reaction is optionally carried out in the presence of an acid-binding agent (proton acceptor). Examples of suitable proton acceptors include alkali metal carbonates and alkali metal bicarbonates, such a sodium carbonate or potassium bicarbonate; tertiary organic amines, such as pyridine, triethylamine, ethyldiisopropylamine, or 4-dimethylaminopyridine; and sodium hydride. The reaction is carried out at temperatures of from about $-25°$ to $130°$ C. in an inert solvent. Examples of suitable inert solvents include chlorinated aliphatic hydrocarbons such as methylene chloride or 1,2-dichloroethane; open-chained or cyclic ethers such as diethyl ether, tetrahydrofuran, or 1,4-dioxane; aromatic hydrocarbons such as benzene, toluene, xylene, or o-dichlorobenzene; polar aprotic solvents such as acetonitrile, dimethylformamide, or hexamethylphosphoric acid triamide; and mixtures thereof. The reaction times are from about 15 minutes to 80 hours, dependent upon the quantity and nature of the acylation agent of Formula III used. It is not necessary to prepare the compounds of Formula III in pure form; instead, they may be produced in situ in the reaction mixture in known manner.

METHOD B

Compounds of Formula I wherein R represents (1-methyl-1,2,5,6-tetrahydro-4-pyridinyl)methyl or 1-methyl-1,2,5,6-tetrahydro-4-pyridinyl, optionally substituted by another methyl group in the heterocyclic six-membered ring, can also be prepared by reacting, in a first step, a thienobenzodiazepinone of Formula II with an acylation agent of the formula

(IV)

wherein Z is as defined above for Formula III and $R_p$ represents an optionally methyl substituted 4-pyridinyl or (4-pyridinyl)methyl, to form an intermediate compound of the formula

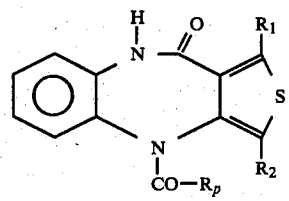
(V)

wherein $R_1$, $R_2$, and $R_p$ are as defined above. Acylation will be successful under the conditions mentioned for Method A, but it is preferable to carry out the reaction in boiling dioxane in the presence of pyridine, 4-dimethylamino-pyridine, or triethylamine.

The compounds of Formula V are then methylated with a methylation agent of the formula

(VI)

wherein X represents the acid group of a strong oxyacid, for example, of sulfuric, methylsulfuric, fluorosulfonic, trifluoromethanesulfonic, methanesulfonic, benzenesulfonic, p-toluenesulfonic, p-bromobenzenesulfonic, or phosphoric acid or a halide, preferably chloride, bromide, or iodide, to form a pyridinium salt of the formula

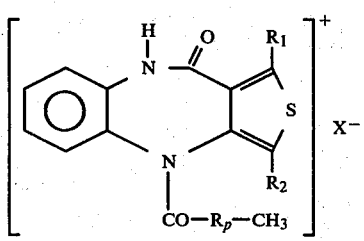
(Va)

wherein $R_1$, $R_2$, $R_p$, and X are as defined above. The methylation is carried out in inert solvent, e.g., a chlorinated aliphatic hydrocarbon, such as methylene chloride, 1,2-dichloroethane; an open-chained or cyclic ether, such as diethyl ether or tetrahydrofuran; or an aromatic hydrocarbon, such as benzene, toluene, xylene, or dichlorobenzene, but preferably in dioxane, acetonitrile, or dimethylformamide, and at temperatures of from about −20° to 130° C., preferably from about 30° to 100° C.

Subsequent reduction of the pyridinium salts of Formula Va with sodium or potassium borohydride or sodium or potassium alkoxyborohydride, dialkoxyborohydride, or trialkoxyborohydride in protic solvents, for example, in water, methanol, ethanol, 2-propanol, or mixtures thereof, at temperatures of from about −40° to 50° C., preferably at 0° C., produces the desired thienobenzodiazepinones of Formula I wherein $R_1$ and $R_2$ have the meanings given above and R represents (1-methyl-1,2,5,6-tetrahydro-4-pyridinyl)methyl or 1-methyl-1,2,5,6-tetrahydro-4-pyridinyl.

The processes for preparing the pharmacologically active thienobenzodiazepinones of Formula I are thus characterized in that thienobenzodiazepinones of Formula II are acylated with compounds of Formula III or with pyridine alkanoic acid derivatives of Formula IV, and then methylated and reduced with borohydrides or alkoxyborohydrides, and optionally the resulting base is subsequently converted into a pharmacologically acceptable acid addition salt or an acid addition salt obtained is converted into the free base or a pharmacologically acceptable acid addition salt using methods known per se.

Some of the thienobenzodiazepinones of Formula I according to the invention contain one or two asymmetric carbon atoms in the R group. These compounds may therefore occur in two diastereomeric cis and trans forms or as the enantiomeric (+) and (−) forms. The invention includes the individual isomers and the mixtures thereof.

The diastereomers may be separated on the basis of their different physico-chemical properties, e.g., by fractional recrystallization from suitable solvents or by chromatographic methods.

Any racemates of the compounds of Formula I may be separated according to known methods, for example, by use of an optically active acid such as (+)- or (−)-tartaric acid or a derivative thereof, such as (+)- or (−)-diacetyl tartaric acid, (+)- or (−)-monomethyl tartrate, or (+)-camphorsulfonic acid.

In a conventional method for separating isomers, the racemate of a compound of Formula I is reacted with an equimolar quantity of one of the above-mentioned optically active acids in a solvent, and the crystalline optically active salts obtained are separated on the basis of their different solubilities. This reaction may be carried out in any type of solvent provided that the salts have sufficiently different solubilities therein. Preferably, methanol, ethanol, or a mixture thereof, for example, in proportions of 50:50 by volume, is used. Then, each of the optically active salts is dissolved in water and neutralized, and in this way the corresponding free compound is obtained in the (+) or (−) form.

The starting compounds of Formula II can be prepared, according to U.S. Pat. No. 3,953,430, incorporated herein by reference, by reacting o-phenylenediamine with a tetrahydrothiophene carboxylic acid derivative of the formula

wherein $R_1$ is as defined above, $R_2'$ represents hydrogen or alkyl having from 1 to 4 carbon atoms, and $R_3$ represents hydrogen or alkyl having from 1 to 5 carbon atoms. The reaction is effected, for example, in an inert solvent such as toluene at temperatures up to the boiling point of the reaction mixture. A tetrahydrothienobenzodiazepinone of the formula

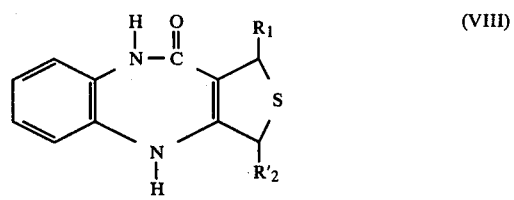

is thus obtained, which is subsequently reacted with a dehydration agent, e.g., N-bromosuccinimide in dimethylformamide, to form the corresponding compounds of Formula II wherein $R_2$ has the meaning of $R_2'$. If it is intended to prepare a compound of Formula II wherein $R_2$ represents halogen, a compound of Formula II wherein $R_2$ represents hydrogen is subsequently halogenated by use of a conventional method.

In accordance with the above-described procedure, compounds such as, for example, the following can be prepared:

(a) 3-chloro-4,9-dihydro-10H-thieno[3,4-b][1,5]benzodiazepin-10-one;
(b) 4,9-dihydro-3-methyl-10H-thieno[3,4-b][1,5]benzodiazepin-10-one, m.p.: 228°–230° C. (methanol);
(c) 4,9-dihydro-1,3-dimethyl-10H-thieno[3,4-b][1,5]benzodiazepin-10-one, m.p.: 195°–196° C.; and
(d) 4,9-dihydro-1-methyl-10H-thieno[3,4-b][1,5]benzodiazepin-10-one, m.p.: 274°–276° C. (n-propanol).

Compounds of Formulae III and IV are known or may readily be obtained, as mentioned above, analogously to known methods of preparation. For example, by reaction of the sodium salt of 4-hydroxy-1-methyl-4-piperidinyl-acetic acid with thionyl chloride, a mixture of 1-methyl-1,2,5,6-tetrahydro-4-pyridinylacetic acid chloride and (1-methyl-4-piperidinylidene)acetyl chloride is obtained, which can be reacted according to Method A, with separation, with a thienobenzodiazepine of Formula II to form a mixture of the desired compounds of Formula I wherein R represents (1-methyl-1,2,-5,6-tetrahydro-4-pyridinyl)methyl and (1-methyl-4-piperidinylidene)methyl. Optionally this mixture of double bond isomers can subsequently be broken down into its components by a known method, for example, fractional crystallization, column chromatography, or high pressure liquid chromatography.

As already mentioned above, the novel compounds of Formula I have valuable pharmacological properties. In particular, they have anti-ulcerogenic effects, they inhibit gastric acid secretion, and they have favorable effects on various other disorders of the gastrointestinal tract, including, in particular, irritable colon.

A favorable relation between anti-ulcerogenic and anti-secretory effects, on the one hand, and the undesirable effects on pupil size and the secretion of tears and saliva, on the other hand, which occurs particularly with therapeutic agents having an anti-cholinergic component, is of particular importance in the therapeutic use of the substances. The following tests show that the compounds according to the invention have surprisingly favorable characteristics in this respect.

1. INVESTIGATION OF THE SELECTIVITY OF THE ANTIMUSCARINIC ACTIVITY

Objects:

Oxotremorine, a specific agonist for muscarinic receptors, produces lesions in the mucous membrane of the stomach in rats and increases their secretion of saliva. This test method was chosen so that any selective activity of an anti-muscarinic substance on the stomach could be identified.

Method:

Ten female albino rats (of the Crl:COBS-CD (SD) BR strain) with a body weight of from 120 to 150 gm apiece were used in each treatment group and were kept without food for 24 hours before the start of the test but given free access to drinking water.

To determine, in preliminary tests, the muscarinic effect of oxotremorine on each of the symptoms studied, a dosage/activity curve was drawn up with at least three dosages for each symptom.

When the antimuscarinic substances were tested, the dosage of oxotremorine which triggered the symptom in question in 90 to 100% of the animals in the preliminary tests was used.

Lesions in mucous membrane of stomach: 0.62 mg/kg i.v.

Secretion of saliva: 0.083 mg/kg i.v.

Each antimuscarinic substance was administered intravenously in uniformly graduated doses 15 minutes before the oxotremorine was administered. Control groups were given corresponding quantities of the solvent and suspension agent instead of the test substance. Immediately after the oxotremorine was administered, the animals were placed in a glass cage for 15 minutes and observed.

The test for the effect on the oxotremorine-induced secretion of saliva was carried out as a blind test, i.e., the tester did not know which treatment the animals had been given.

The results were expressed as the percentage inhibition of the oxotremorine effect (the percentage of animals which did not show the symptom in question). The $ED_{50}$ values were determined using the method described by LITCHFIELD and WILCOXON (J. Pharmacol. Exp. Ther. 96, 99, 1949).

The effects on lesions of the mucous membrane of the stomach were evaluated as follows:

The lesions of the gastric mucous membrane were produced by intravenous injection of 0.62 mg/kg of oxotremorine 30 minutes after oral administration of 1 mg/kg of neostigmine (a cholinesterase inhibitor). Sixty minutes after the administration of the neostigmine, the animals were killed, and the stomachs were removed, opened, and examined for the presence of any lesions in the mucous membrane. The protective effect of the test substances was expressed as the percentage inhibition (percentage of animals without lesions). The $ED_{50}$ and $ED_{70}$ values were determined using the method of LITCHFIELD and WILCOXON (see above).

2. TESTING FOR MYDRIASIS

The effect of the test substances on the pupil size in rats was investigated as follows:

The substances were administered intravenously to groups of 10 animals in at least three uniformly graduated doses. The pupil size was then observed for 10 minutes to see if there were any changes (mydriasis or miosis). Again, the test was carried out blind, i.e., the tester did not know what preliminary treatment the animals had received. The percentage of test animals in which mydriasis occurred was determined. The $ED_{50}$ values were again determined using the method of LITCHFIELD and WILCOXON (see above).

3. STUDIES OF BINDING TO MUSCARINIC RECEPTORS: DETERMINATION OF THE $IC_{50}$ VALUE

The organ donors were male Sprague-Dawley rats with a body weight of from about 180 to 220 gm each. After the heart, stomach, and cerebral cortex had been removed, the remainder of the operation was carried out in ice-cold Hepes-HCl buffer (pH 7.4; 100 m molar NaCl, 10 m molar $MgCl_2$). The smooth muscle of the fundus of the stomach was separated from the mucous membrane of the stomach and subjected to preliminary homogenization. The whole heart was cut up with scissors. All the organs were then homogenized in a Potter apparatus.

For the binding test, the homogenized organs were diluted as follows:

Smooth muscle of the fundus of the stomach: 1:100
Whole heart: 1:250
Cerebral cortex: 1:3000

The homogenized organ preparations were incubated at a specific concentration of the radioligand and with a series of concentrations of the non-radioactive test substances in an Eppendorf centrifuge tube at 30° C. The duration of incubation was 45 minutes. The substance 0.3 n molar $^3$H-N-methylscopolamine ($^3$H-NMS) was used as the radioligand. After incubation had been brought to an end by centrifuging at 14000 g, the radioactivity in the pellet was determined. It represents the sum of the specific and non-specific binding of $^3$H-NMS. The proportion of non-specific binding was defined as the radioactivity which was bound in the presence of 1$\mu$ molar quinuclidinylbenzylate. Four measurements were taken in each case. The $IC_{50}$ values of the non-labelled test substances were determined graphically. They represent the concentration of test substance at which the specific binding of $^3$H-NMS to the muscarinic receptors in the various organs was inhibited by 50%.

The following compound, an example of a compound of Formula I, was tested as described above:

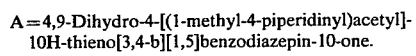

A=4,9-Dihydro-4-[(1-methyl-4-piperidinyl)acetyl]-10H-thieno[3,4-b][1,5]benzodiazepin-10-one.

The testing results are set forth in the following table:

TABLE

| Substance | Receptor Binding Tests IC$_{50}$ [n Mol l$^{-1}$] | | Oxotremorine Test [μg/kg] i.v. | | | Mydriasis ED$_{50}$ i.v. [μg/kg] |
|---|---|---|---|---|---|---|
| | Cortex | Smooth Muscle Fundus of Stomach | Anti-ulcerative Effect ED$_{50}$ | ED$_{70}$ | Inhibition of Salivation ED$_{50}$ | |
| A | 20 | 75 | 7.8 | 14 | 21.5 | 30 |

The results in the above table show that the compounds mentioned generally have a high affinity with muscarinic receptors. Moreover, the results show that the novel compounds of Formula I differentiate between muscarinic receptors in different types of tissue. This is clear from the considerably lower IC$_{50}$ values in the tests on preparations from the cerebral cortex compared with those of the smooth muscle of the stomach.

The pharmacological data in the above table show—in complete agreement with the receptor binding studies—that the formation of oxotremorine-induced lesions in the mucous membrane of the stomach is inhibited by the above-mentioned compounds even at doses at which no restriction of salivation and no mydriasis can be observed.

The following examples are intended to illustrate the invention and should not be construed as limiting the invention thereto. In the examples, "M.p." or "m.p." indicates "melting point" and "D" indicates "decomposition".

EXAMPLES

Example 1

4,9-Dihydro-4-[(1-methyl-4-piperidinyl)acetyl]-10H-thieno-[3,4-b][1,5]benzodiazepin-10-one A solution of 2.2 gm (0.01 mol) of 4,9-dihydro-10H-thieno[3,4-b][1,5]benzodiazepin-10-one in 50 ml of dioxane and 10 ml of pyridine was mixed at ambient temperature with a solution of 0.02 mol of (1-methyl-4-piperidinyl) acetyl chloride (prepared from the potassium salt of 1-methyl-4-piperidinylacetic acid by reaction with thionyl chloride) in 100 ml of dioxane. The mixture was heated at 40° C. for three hours, with stirring, and then at 80° C. for two hours. After the dioxane solution was poured off, the viscous residue was taken up in water, the resulting mixture was filtered, and the filtrate was rendered alkaline and extracted with methylene chloride. The extraction residue was purified by column chromatography [silica gel, eluant: ethyl acetate/methylene chloride (1:1); then with methylene chloride/cyclohexane/methanol/ammonia (102:23:23:3) as eluant]. The desired fraction was concentrated by evaporation in vacuo and the residue was recrystallized from ethyl acetate.

M.p.: 184°–185° C.
Yield: 28% of theory.
C$_{19}$H$_{21}$N$_3$O$_2$S (355.4)—Calculated: C, 64.24; H, 5.91; N, 11.82; S, 9.00. Found: C, 64.26; H, 5.92; N, 12.02; S, 9.14.

By use of procedures analogous to that described above, the following compounds were prepared:

(a) 4,9-dihydro-1-methyl-4-[(1-methyl-4-piperidinyl)acetyl]-10H-thieno[3,4-b][1,5]benzodiazepin-10-one, prepared from 4,9-dihydro-1-methyl-10H-thieno[3,4-b][1,5]-benzodiazepin-10-one and (1-methyl-4-piperidinyl)acetyl bromide;

(b) 4,9-dihydro-3-methyl-4-[(1-methyl-4-piperidinyl)acetyl]-10H-thieno[3,4-b][1,5]benzodiazepin-10-one, m.p.: 192°–193° C. (acetonitrile), prepared from 4,9-dihydro-3-methyl-10H-thieno[3,4-b][1,5]benzodiazepin-10-one and (1-methyl-4-piperidinyl)acetyl chloride;

(c) 4,9-dihydro-1,3-dimethyl-4-[(1-methyl-4-piperidinyl)-acetyl]-10H-thieno[3,4-b][1,5]benzodiazepin-10-one, prepared from 4,9-dihydro-1,3-dimethyl-10H-thieno[3,4-b][1,5]-benzodiazepin-10-one and (1-methyl-4-piperidinyl)acetyl chloride;

(d) 3-chloro-4,9-dihydro-4-[(1-methyl-4-piperidinyl)acetyl]-10H-thieno[3,4-b][1,5]benzodiazepin-10-one, prepared from 3-chloro-4,9-dihydro-10H-thieno[3,4-b][1,5]benzodiazepin-10-one and (1-methyl-4-piperidinyl)acetyl chloride;

(e) 4,9-dihydro-4-[(1-methyl-1,2,5,6-tetrahydro-4-pyridinyl)-acetyl]-10H-thieno[3,4-b][1,5]benzodiazepin-10one, prepared from 4,9-dihydro-10H-thieno[3,4-b][1,5]benzodiazepin-10-one and (1-methyl-1,2,5,6-tetrahydro-4-pyridinyl)-acetyl chloride;

(f) 4,9-dihydro-4-[(1-methyl-4-piperidinyliden)acetyl]-10H-thieno[3,4-b][1,5]benzodiazepin-10-one, prepared from 4,9-dihydro-10H-thieno[3,4-b][1,5]benzodiazepin-10-one and (1-methyl-4-piperidinyliden)acetyl chloride;

(g) 4,9-dihydro-4-[(1-methyl-1,2,5,6-tetrahydro-4-pyridinyl)-carbonyl]-10H-thieno[3,4-b][1,5]benzodiazepin-10-one, m.p.: 210°–212° C. (acetonitrile), prepared from 4,9-dihydro-10H-thieno[3,4-b][1,5]benzodiazepin-10-one and 1-methyl-1,2,5,6-tetrahydro-isonicotinic acid chloride hydrochloride;

(h) 4,9-dihydro-1-methyl-4-[(1-methyl-1,2,5,6-tetrahydro-4-pyridinyl)carbonyl]-10H-thieno[3,4-b][1,5]benzodiazepin-10-one, prepared from 4,9-dihydro-1-methyl-10H-thieno[3,4-b][1,5]benzodiazepin-10-one and 1-methyl-1,2,5,6-tetrahydro-isonicotinic acid chloride hydrochloride;

(i) 4,9-dihydro-3-methyl-4-[(1-methyl-1,2,5,6-tetrahydro-4-pyridinyl)carbonyl]-10H-thieno[3,4-b][1,5]benzodiazepin-10-one, prepared from 4,9-dihydro-3-methyl-10H-thieno[3,4-b][1,5]-benzodiazepin-10-one and 1-methyl-1,2,5,6-tetrahydro-isonicotinic acid chloride hydrochloride [H. Leditschke, Arch. Pharm., 295, 328 (1962)];

(j) 4,9-dihydro-1,3-dimethyl-4-[(1-methyl-1,2,5,6-tetrahydro-4-pyridinyl)carbonyl]-10H-thieno[3,4-b][1,5]benzodiazepin-10-one, prepared from 4,9-dihydro-1,3-dimethyl-10H-thieno[3,4-b][1,5]-benzodiazepin-10-one and 1-methyl-1,2,5,6-tetrahydro-isonicotinic acid chloride hydrochloride;

(k) 3-chloro-4,9-dihydro-4-[(1-methyl-1,2,5,6-tetrahydro-4-pyridinyl)carbonyl]-10H-thieno[3,4-b][1,5]benzodiazepin-10-one, prepared from 3-chloro-4,9-dihydro-10H-thieno[3,4-b][1,5]benzodiazepin-10-one and 1-methyl-1,2,5,6-tetrahydro-isonicotinic acid chloride hydrochloride;

(l) a mixture of diastereomers of 4,9-dihydro-4-[(8-methyl-8-azabicyclo[3.2.1]oct-3-yl)acetyl]-10H-thieno[3,4-b]-[1,5]benzodiazepin-10-one, prepared from 4,9-dihydro-10H-thieno[3,4-b][1,5]benzodiazepin-10-one and (8-methyl-8-azabicyclo[3.2.1]oct-3-yl)acetyl chloride;

(m) a mixture of diastereomers of 4,9-dihydro-1-methyl-4-[(8-methyl-8-azabicyclo[3.2.1]oct-3-yl)acetyl]-10H-thieno[3,4-b][1,5]benzodiazepin-10-one, prepared from 4,9-dihydro-1-methyl-10H-thieno[3,4-b][1,5]benzodiazepin-10-one and (8-methyl-8-azabicyclo[3.2.1]oct-3-yl)-acetyl chloride;

(n) a mixture of diastereomers of 4,9-dihydro-3-methyl-4-[(8-methyl-8-azabicyclo[3.2.1]oct-3-yl)acetyl]-10H-thieno[3,4-b][1,5]benzodiazepin-10-one, prepared from 4,9-dihydro-3-methyl-10H-thieno[3,4-b][1,5]benzodiazepin-10-one and (8-methyl-8-azabicyclo]3.2.1]oct-3-yl)-acetyl chloride;

(o) a mixture of diastereomers of 4,9-dihydro-1,3-dimethyl-4-[(8-methyl-8-azabicyclo[3.2.1]oct-3-yl)acetyl]-10H-thieno[3,4-b][1,5]benzodiazepin-10-one, prepared from 4,9-dihydro-1,3-dimethyl-10H-thieno[3,4-b][1,5]-benzodiazepin-10-one and (8-methyl-8-azabicyclo[3.2.1]oct-3-yl)acetyl chloride; and (p) a mixture of diastereomers of 3-chloro-4,9-dihydro-4-[(8-methyl-8-azabicyclo[3.2.1]oct-3-yl)acetyl]-10H-thieno[3,4-b][1,5]benzodiazepin-10-one, prepared from 3-chloro-4,9-dihydro-10H-thieno[3,4-b][1,5]benzodiazepin-10-one and (8-methyl-8-azabicyclo[3.2.1]oct-3-yl)-acetyl chloride.

Example 2

4,9-Dihydro-4-[(1-methyl-1,2,5,6-tetrahydro-4-pyridinyl)carbonyl]-10H-thieno[3,4-b][1,5]benzodiazepin-10-one (a) A mixture of 12.9 gm (0.06 mol) of 4,9-dihydro-10H-thieno[3,4-b][1,5]benzodiazepin-10-one, 11.7 gm of (0.066 mol) of isonicotinic acid chloride hydrochloride, 10.3 gm of pyridine (0.13 mol), and 250 ml of dioxane was refluxed for six hours. After the mixture had been separated from the solvent by decanting the viscous residue was taken up in water and filtered. The filtrate was rendered alkaline with sodium carbonate. 4,9-Dihydro-isonicotinoyl-10H-thieno-[3,4-b][1,5]benzodiazepin-10-one was precipitated and, after crystallization from ethyl acetate, it was found to have a melting point of 282°–284° C.

Yield: 40% of theory.

(b) A quantity of 2.4 gm (0.0074 mol) of 4,9-dihydro-4-isonicotinoyl-10H-thieno[3,4-b][1,5]benzodiazepin-10-one were dissolved in 30 ml of dimethylformamide. After addition of 2 ml of methyl iodide, the mixture was stirred for three hours at ambient temperature. Then, it was concentrated by evaporation in vacuo. The result was 3.4 gm of the methoiodide, m.p.: 295° C. (D).

(c) 4,9-Dihydro-4-isonicotinoyl-10H-thieno[3,4-b][1,5]benzodiazepin-10-one methoiodide in an amount of 3.4 gm (0.0073 mol) was suspended in 40 ml of methanol, and at 0° C. 0.5 gm (0.014 mol) of sodium borohydride were added in portions. After the development of hydrogen ceased, the mixture was stirred for a further two hours in an ice bath. Then, 100 ml of ice-water was added, the mixture was filtered, and the filtrate was extracted with methylene chloride. The extraction residue was recrystallized from acetonitrile. 4,9-Dihydro-4-[(1-methyl-1,2,5,6-tetrahydro-4-pyridinyl)carbonyl]-10H-thieno[3,4-b][1,5]benzodiazepin-10-one was obtained, m.p.: 210°–212° C., in a yield of 35% of theory.

The base obtained was dissolved in ethyl acetate and mixed with a solution of hydrogen chloride in dioxane. The hydrochloride precipitated was recrystallized from ethanol; m.p.: 215°–217° C. (D).

By use of procedures analogous to that described above, the following compounds were prepared:

(a) 4,9-dihydro-4-[(1-methyl-1,2,5,6-tetrahydro-4-pyridinyl)acetyl]-10H-thieno[3,4-b][1,5]benzodiazepin-10-one, prepared from 4,9-dihydro-10H-thieno[3,4-b][1,5]benzodiazepin-10-one and 4-pyridinoacetic acid chloride hydrochloride via 4,9-dihydro-4-[(4-pyridinyl)acetyl]-10H-thieno-[3,4-b][1,5]benzodiazepin-10-one and 4,9-dihydro-4-[(4-pyridinyl)acetyl]-10H-thieno[3,4-b][1,5]benzodiazepin-10-one methoiodide;

(b) 4,9-dihydro-1-methyl-4-[(1-methyl-1,2,5,6-tetrahydro-4-pyridinyl)carbonyl]-10H-thieno[3,4-b][1,5]benzodiazepin-10-one, prepared from 4,9-dihydro-1-methyl-10H-thieno[3,4-b][1,5]-benzodiazepin-10-one and isonicotinic acid chloride hydrochloride via 4,9-dihydro-1-methyl-4-[(4-pyridinyl)carbonyl]-10H-thieno[3,4-b][1,5]benzodiazepin-10-one and 4,9-dihydro-1-methyl-4-[(4-pyridinyl)carbonyl]-10H-thieno[3,4-b][1,5]-benzodiazepin-10-one methoiodide;

(c) 4,9-dihydro-3-methyl-4-[(1-methyl-1,2,5,6-tetrahydro-4-pyridinyl)carbonyl]-10H-thieno[3,4-b][1,5]benzodiazepin-10-one, prepared from 4,9-dihydro-3-methyl-10H-thieno[3,4-b][1,5]-benzodiazepin-10-one and isonicotinic acid chloride hydrochloride via 4,9-dihydro-3-methyl-4-[(4-pyridinyl)carbonyl]-10H-thieno[3,4-b][1,5]benzodiazepin-10-one and 4,9-dihydro-3-methyl-4-[(4-pyridinyl)carbonyl]-10H-thieno[3,4-b][1,5]-benzodiazepin-10-one methoiodide;

(d) 4,9-dihydro-1,3-dimethyl-4-[(1-methyl-1,2,5,6-tetrahydro-4-pyridinyl)carbonyl]-10H-thieno[3,4-b][1,5]benzodiazepin-10-one, prepared from 4,9-dihydro-1,3-dimethyl-10H-thieno[3,4-b][1,5]-benzodiazepin-10-one and isonicotinic acid chloride hydrochloride via 4,9-dihydro-1,3-dimethyl-4-[(4-pyridinyl)carbonyl]-10H-thieno[3,4-b][1,5]benzodiazepin-10-one and 4,9-dihydro-1,3-dimethyl-4-[(4-pyridinyl)carbonyl]-10H-thieno-[3,4-b][1,5]benzodiazepin-10-one methoiodide; and (e) 3-chloro-4,9-dihydro-4-[(1-methyl-1,2,5,6-tetrahydro-4-pyridinyl)carbonyl]-10H-thieno[3,4-b][1,5]benzodiazepin-10-one, prepared from 3-chloro-4,9-dihydro-10H-thieno[3,4-b][1,5]benzodiazepin-10-one and isonicotinic acid chloride hydrochloride via 3-chloro-4,9-dihydro-4-[(4-pyridinyl)carbonyl]-10H-thieno[3,4-b][1,5]benzodiazepin-10-one and 3-chloro-4,9-dihydro-4-[(4-pyridinyl)carbonyl]-10H-thieno[3,4-b][1,5]benzodiazepin-10-one methoiodide.

Example 3

4,9-Dihydro-4-[(1-methyl-4-piperidinyl)acetyl]-10H-thienobenzodiazepin-10-one

A mixture of 0.983 gm (6.25 mmol) of 1-methyl-4-piperidinyl acetic acid and 0.20 gm (6.25 mmol) of 75% sodium hydride (in paraffin oil) was heated in 16 ml of dimethylformamide at 50° to 80° C. until the development of hydrogen ceased (2 to 3 hours). To the sodium salt of the acid formed, 1.35 gm (6.24 mmol) of 4,9-dihydro-10H-thieno[3,4-b]-[1,5]benzodiazepin-10-one was added and, at −10° C., 0.99 gm of 98% phosphorus oxychloride were added dropwise over a period of ten minutes. The resulting mixture was stirred at −10° C. for four hours, at 0° C. for four hours, and at ambient temperature for twenty hours. The mixture was poured onto ice, adjusted to a pH of 3.5 with sodium hydroxide solution, and extracted with methylene chloride. The aqueous phase was adjusted to a pH of 9 and extracted with methylene chloride again. The organic phase was washed with water and concentrated by evaporation in vacuo. An amount of 0.59 gm (27% of theory) of 4,9-dihydro-4-[(1-methyl-4-piperidinyl)acetyl]-10H-thieno[3,4-b][1,5]benzodiazepin-10-one was obtained, m.p.: 184°–185° C. (ethyl acetate).

By use of procedures analogous to that described above, the following compounds were prepared:

(a) 4,9-dihydro-4-[(1-methyl-4-piperidinylidene)acetyl]-10H-thieno[3,4-b][1,5]benzodiazepin-10-one, prepared from 4,9-dihydro-10H-thieno[3,4-b][1,5]benzodiazepin-10-one and (1-methyl-4-piperidinylidene)acetic acid;

(b) 4,9-dihydro-4-[(1-methyl-1,2,5,6-tetrahydro-4-pyridinyl)-acetyl]-10H-thieno[3,4-b][1,5]benzodiazepin-10-one, prepared from 4,9-dihydro-10H-thieno[3,4-b][1,5]benzodiazepin-10-one and 1-methyl-1,2,5,6-tetrahydro-4-pyridinylacetic acid;

(c) 4,9-dihydro-4-[(1-methyl-1,2,5,6-tetrahydro-4-pyridinyl)-carbonyl]-10H-thieno[3,4-b][1,5]benzodiazepin-10-one, m.p.: 210°–212° C. (acetonitrile), prepared from 4,9-dihydro-10H-thieno[3,4-b][1,5]benzodiazepin-10-one and 1-methyl-1,2,5,6-tetrahydro-isonicotinic acid;

(d) 4,9-dihydro-1-methyl-4-[(1-methyl-4-piperidinyl)acetyl]-10H-thieno[3,4-b][1,5]benzodiazepin-10-one, prepared from 4,9-dihydro-1-methyl-10H-thieno[3,4-b][1,5]benzodiazepin-10-one and (1-methyl-4-piperidinyl)acetic acid;

(e) 4,9-dihydro-4-[(1,3-dimethyl-4-piperidinyl)acetyl]-10H-thieno[3,4-b][1,5]benzodiazepin-10-one (mixture of 2 diastereomers), prepared from 4,9-dihydro-10H-thieno[3,4-b][1,5]benzodiazepin-10-one and (1,3-dimethyl-4-piperidinyl)acetic acid; and (f) 4,9-dihydro-4-[(8-methyl-8-azabicyclo[3.2.1]oct-3-yl)-acetyl]-10H-thieno[3,4-b][1,5]benzodiazepin-10-one, (mixture of 2 diastereomers), prepared from 4,9-dihydro-10H-thieno[3,4-b][1,5]benzodiazepin-10-one and (8-methyl-8-azabicyclo[3.2.1]oct-3-yl)acetic acid.

Example 4

4,9-Dihydro-4-[(1-methyl-4-piperidinyl)acetyl]-10H-thieno-[3,4-b][1,5]benzodiazepin-10-one A quantity of 1.1 gm of ethyl chloroformate was added dropwise at 0° C. at a suspension of 1.57 gm (10 mmol) of 1-methyl-4-piperidinyl)acetic acid in 20 ml of tetrahydrofuran. Then, 2.16 gm (10 mmol) of 4,9-dihydro-10H-thieno-[3,4-b][1,5]benzodiazepin-10-one were added to the resulting suspension, which was then stirred for one hour at 0° C. and for a further four hours at ambient temperature. The suspension was then poured onto 160 ml of 2 N sodium hydroxide solution and extracted with toluene, and the organic phase was concentrated to dryness. After purification by column chromatography [silica gel; dioxane/methanol (1:1)], 4,9-dihydro-4-[(1-methyl-4-piperidinyl)-acetyl]-10H-thieno[3,4-b][1,5]benzodiazepin-10-one was obtained, m.p.: 184°–185° C. (ethyl acetate).

Yield: 0.84 gm (24% of theory).

By use of a procedure analogous to that described above, 4,9-dihydro-4-[(1-methyl-1,2,5,6-tetrahydro-4-pyridinyl)carbonyl]-10H-thieno[3,4-b][1,5]benzodiazepin-10-one, m.p.: 210°–212° C. (acetonitrile), was prepared from 4,9-dihydro-10H-thieno[3,4-b][1,5]benzodiazepin-10-one and 1-methyl-1,2,5,6-tetrahydro-isonicotinic acid.

Example 5 endo-4,9-Dihydro-4-[(8-methyl-8-azabicyclo[3.2.1]oct-3-yl)-acetyl]-10H-thieno[3,4-b][1,5]benzodiazepin-10-one The above compound was prepared analogously to Example 1 from 4,9-dihydro-10H-thieno[3,4-b][1,5]benzodiazepin-10-one and (endo-8-methyl-8-azabicyclo[3.2.1]oct-3-yl)acetyl chloride in a yield of 14% of theory. Colorless crystals, m.p.: 167°–168° C. (acetonitrile).

$C_{21}H_{23}N_3O_2S$ (381.49)— Calculated: C, 66.12; H, 6.08; N, 11.01; S, 8.40. Found: C, 66.16; H, 5.93; N, 11.18; S, 8.47.

IR ($CH_2Cl_2$): NH 3365/cm; CO 1665/cm (broad).

UV (ethanol): Shoulder at 250 nm (E=0.15).

UV (ethanol/KOH): Shoulder at 252 nm (E=0.16); Shoulder at 284 nm (E=0.08) (c=50 mg/l, layer thickness: 2 mm).

$^1$H-NMR ($CDCl_3/D_2O$): δ=8.09 (1H-d; J=2.4 Hz; 1-H); 7.0–7.5 (5H-m; ar. H); 2.8–3.2 (2H-m); 2.4–2.7 (2H-m); 1.7–2.3 (5H-m); 2.18 (3H-s; N-CH$_3$); 0.8–1.5 ppm (4H-m).

The following examples are illustrative of a few pharmaceutical dosage unit compositions comprising compounds of the invention as active ingredient.

Example 6

Tablets containing 5 mg of 4,9-Dihydro-4-[(1-methyl-4-piperidinyl)acetyl]-10H-thieno[3,4-b][1,5]benzodiazepin-10-one Each tablet is compounded from the following ingredients:

| Component | Amount (mg) |
| --- | --- |
| Active ingredient | 5.0 |
| Lactose | 148.0 |
| Potato starch | 65.0 |
| Magnesium stearate | 2.0 |
| Total: | 220.0 |

Preparation:

A 10% mucilage is prepared from potato starch by heating. The active ingredient lactose, and remaining potato starch are mixed together and granulated with the mucilage through a screen with a mesh size of 1.5 mm. The granulate is dried at 45° C., passed through the screen again, mixed with magnesium stearate, and compressed to form tablets.

Weight of tablet: 220 mg.
Punch: 9 mm.

Example 7

Coated tablets containing 5 mg of 4,9-Dihydro-4-[(1-methyl-4-piperidinyl)acetyl]-10H-thieno[3,4-b][1,5]benzodiazepin-10-one The tablets prepared according to Example 6 are coated by a known method with a shell consisting essentially of sugar and talc. The finished coated tablets are polished with beeswax.

Weight of coated tablet: 300 mg.

Example 8

Ampules containing 1 mg of
4,9-Dihydro-4-[(1-methyl-1,2,5,6-tetrahydro-4-piperidinyl)carbonyl]-10H-thieno[3,4-b][1,5]benzodiazepin-10-one-hydrochloride Each ampule contains a solution having the following composition:

| Component | | Amount |
|---|---|---|
| Active ingredient | | 1.0 mg |
| Sodium chloride | | 8.0 mg |
| Distilled water | q.s. ad | 1 ml |

Preparation:
The active ingredient and sodium chloride are dissolved in distilled water and then topped up to the volume given. The solution is sterilized by filtration and transferred into 1 ml ampules.
Sterilization: 20 minutes at 120° C.

Example 9

Suppositories containing 5 mg of
4,9-Dihydro-4-[(1-methyl-4-piperidinyl)acetyl]-10H-thieno[3,4-b][1,5]benzodiazepin-10-one Each suppository has the following composition:

| Component | Amount (mg) |
|---|---|
| Active ingredient | 5.0 |
| Suppository mass (e.g., WITEPSOL ® W 45, available from Chemische Werke Witten GmbH). | 1 695.0 |
| TOTAL: | 1 700.0 |

Preparation:
The finely powdered active ingredient is suspended in the molten suppository mass, which has been cooled to 40° C. At 37° C. the mass is poured into slightly chilled suppository molds.
Weight of suppository: 1.7 gm.

Example 10

Drops containing
4,9-Dihydro-4-[(1-methyl-1,2,5,6-tetrahydro-4-pyridinyl)carbonyl]-10H-thieno[3,4-b][1,5]benzodiazepin-10-one hydrochloride (5 mg/ml)

One hundred milliliters of drop solution have the following composition:

| Component | | Amount |
|---|---|---|
| Active ingredient | | 0.5 gm |
| Methyl p-hydroxybenzoate | | 0.035 gm |
| Propyl p-hydroxybenzoate | | 0.015 gm |
| Anise oil | | 0.5 gm |
| Menthol | | 0.06 gm |
| Pure ethanol | | 10.0 gm |
| Sodium cyclamate | | 1.0 gm |
| Glycerol | | 15.0 gm |
| Distilled water | q.s. ad | 100.0 ml |

Preparation:
The active ingredient and sodium cyclamate are dissolved in about 70 ml of water, and glycerol is added thereto. The p-hydroxybenzoates, anise oil, and menthol are dissolved in the ethanol, and this solution is added to the aqueous solution, with stirring. Finally, the mixture is made up to 100 ml with water and filtered to remove any suspended particles.

Any one of the other compounds embraced by Formula I, or a combination thereof, may be substituted for the particular active ingredient employed in Examples 6 through 10. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to those particular embodiments, and the various changes and modifications may be made without departing from the spirit of the invention or the scope of the appended claims.

We claim:
1. A compound of the formula

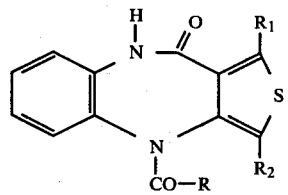

wherein
$R_1$ is hydrogen or alkyl having from 1 to 4 carbon atoms;
$R_2$ is hydrogen, halogen, or alkyl having from 1 to 4 carbon atoms; and
R is (1-methyl-4-piperidinyl)methyl, (1-methyl-1,2,5,6-tetrahydro-4-pyridinyl)methyl, 1-methyl-1,2,5,6-tetrahydro-4-pyridinyl, (1-methyl-4-piperidinylidene)-methyl, or (8-methyl-8-azabicyclo[3.2.1]oct-3-yl)-methyl, each of which can optionally have an additional methyl substituent on the heterocyclic ring,
a diastereoisomer or enantiomer thereof, or a non-toxic, pharmacologically acceptable acid addition salt thereof with an inorganic or organic acid.

2. A compound of claim 1, wherein
$R_1$ and $R_2$, which may be the same or different from each other, are each hydrogen or methyl, and
R is (1-methyl-4-piperidinyl)-methyl, 1-methyl-1,2,5,6-tetrahydro-4-pyridinyl, or (8-methyl-8-azabicyclo[3.2.1]oct-3-yl)methyl,
a diastereoisomer or enantiomer thereof, or a non-toxic, pharmacologically acceptable acid addition salt thereof with an inorganic or organic acid.

3. 4,9-Dihydro-4-[(1-methyl-4-piperidinyl)-acetyl]-10H-thieno[3,4-b][1,5]benzodiazepin-10-one or a non-toxic, pharmacologically acceptable acid addition salt thereof with an inorganic or organic acid.

4. An anti-ulcerogenic pharmaceutical composition consisting essentially of an inert pharmaceutical carrier and an effective anti-ulcerogenic amount of a compound of claim 1.

5. The method of inhibiting the formation of gastric ulcers in a warm-blooded animal in need thereof, which comprises perorally, parenterally, or rectally administering to said animal an effective anti-ulcerogenic amount of a compound of claim 1.

* * * * *

UNITED STATES PATENT AND TRADEMARK OFFICE
CERTIFICATE OF CORRECTION

PATENT NO. : 4,424,225

DATED : January 3, 1984

INVENTOR(S) : GÜNTHER SCHMIDT et al.

It is certified that error appears in the above-identified patent and that said Letters Patent are hereby corrected as shown below:

Column 1, line 42; "gastic" should read -- gastric --.

Column 3, line 54, "8azabicyclo" should read -- 8-azabicyclo --.

Signed and Sealed this

Nineteenth Day of June 1984

[SEAL]

Attest:

*Attesting Officer*

GERALD J. MOSSINGHOFF

*Commissioner of Patents and Trademarks*